(12) United States Patent
Hartmann

(10) Patent No.: US 7,632,293 B2
(45) Date of Patent: Dec. 15, 2009

(54) DYNAMIC DAMPING ELEMENT FOR TWO BONES

(75) Inventor: Stephan Hartmann, Solothurn (CH)

(73) Assignee: Synthes USA, LLC, West Chester, PA (US)

( * ) Notice: Subject to any disclaimer, the term of this patent is extended or adjusted under 35 U.S.C. 154(b) by 736 days.

(21) Appl. No.: 11/393,485

(22) Filed: Mar. 29, 2006

(65) Prior Publication Data
US 2006/0264940 A1 Nov. 23, 2006

Related U.S. Application Data

(63) Continuation of application No. PCT/CH03/00649, filed on Sep. 29, 2003.

(51) Int. Cl.
*A61B 17/70* (2006.01)

(52) U.S. Cl. ............... 606/257; 606/254; 606/255; 606/259; 606/261; 248/560; 267/136; 403/225

(58) Field of Classification Search ........... 606/255, 606/259, 283, 70, 71, 254, 257, 261; 248/560; 267/136; 403/225–227, 229, 347
See application file for complete search history.

(56) References Cited

U.S. PATENT DOCUMENTS

| | | | |
|---|---|---|---|
| 5,011,497 A | 4/1991 | Persson et al. ............ 623/21 |
| 5,375,823 A | 12/1994 | Navas | |
| 5,540,688 A | 7/1996 | Navas | |
| 5,562,737 A | 10/1996 | Graf ...................... 623/17 |
| 5,645,599 A | 7/1997 | Samani | |
| 6,241,730 B1 | 6/2001 | Alby ..................... 606/61 |
| 6,267,764 B1 | 7/2001 | Elberg | |
| 6,293,949 B1 | 9/2001 | Justis et al. ............. 606/61 |
| 6,440,169 B1 | 8/2002 | Elberg et al. | |
| 6,554,831 B1 | 4/2003 | Rivard et al. | |
| 6,761,719 B2 | 7/2004 | Justis et al. ............. 606/61 |
| 2004/0049189 A1 | 3/2004 | Le Couedic et al. ...... 606/61 |
| 2004/0049190 A1 | 3/2004 | Biedermann et al. ...... 606/61 |
| 2004/0267260 A1 | 12/2004 | Mack et al. ............. 606/61 |
| 2005/0049708 A1 | 3/2005 | Atkinson et al. ....... 623/17.16 |
| 2005/0065516 A1 | 3/2005 | Jahng .................... 606/61 |
| 2005/0165396 A1 | 7/2005 | Fortin et al. ............ 606/61 |

(Continued)

FOREIGN PATENT DOCUMENTS

CN 88 2 01056 U 8/1988

(Continued)

*Primary Examiner*—Eduardo C Robert
*Assistant Examiner*—Julianna N Harvey
(74) *Attorney, Agent, or Firm*—Stroock & Stroock & Lavan LLP

(57) ABSTRACT

A damping element for the dynamic stabilization of two bones, particularly of two adjacent bodies of the vertebra, includes a flexible spring element having a hollow space. The hollow space is open on a first end and closed on a second end by a wall extending transversely to the longitudinal axis of the damping element. A clamping sleeve is inserted at least partially into the hollow space. The sleeve has a front end directed towards the wall of the flexible spring element. The distance between the front end and the wall affects the damping characteristics of the damping element. A coaxial connecting element is attached to each end of the flexible spring element. Each connecting element is configured to be connected within an osteosynthetic stabilizing device.

7 Claims, 2 Drawing Sheets

U.S. PATENT DOCUMENTS

| | | | |
|---|---|---|---|
| 2005/0171539 A1 | 8/2005 | Braun et al. | 606/61 |
| 2005/0171543 A1 | 8/2005 | Timm et al. | 606/61 |
| 2005/0177156 A1 | 8/2005 | Timm et al. | 606/61 |
| 2005/0177157 A1 | 8/2005 | Jahng | 606/61 |
| 2005/0182409 A1 | 8/2005 | Callahan et al. | 606/72 |
| 2005/0203513 A1 | 9/2005 | Jahng et al. | 606/61 |
| 2005/0261685 A1 | 11/2005 | Fortin et al. | 606/61 |
| 2005/0288670 A1 | 12/2005 | Panjabi et al. | 606/61 |
| 2005/0288672 A1 | 12/2005 | Ferree | 606/61 |
| 2006/0149238 A1 | 7/2006 | Sherman et al. | 606/61 |

FOREIGN PATENT DOCUMENTS

| | | |
|---|---|---|
| FR | 2 774 581 | 8/1999 |
| FR | 2 812 186 | 2/2002 |
| FR | 2 827 498 | 1/2003 |
| WO | WO 02/07622 | 1/2002 |
| WO | WO 2006/037384 | 4/2006 |

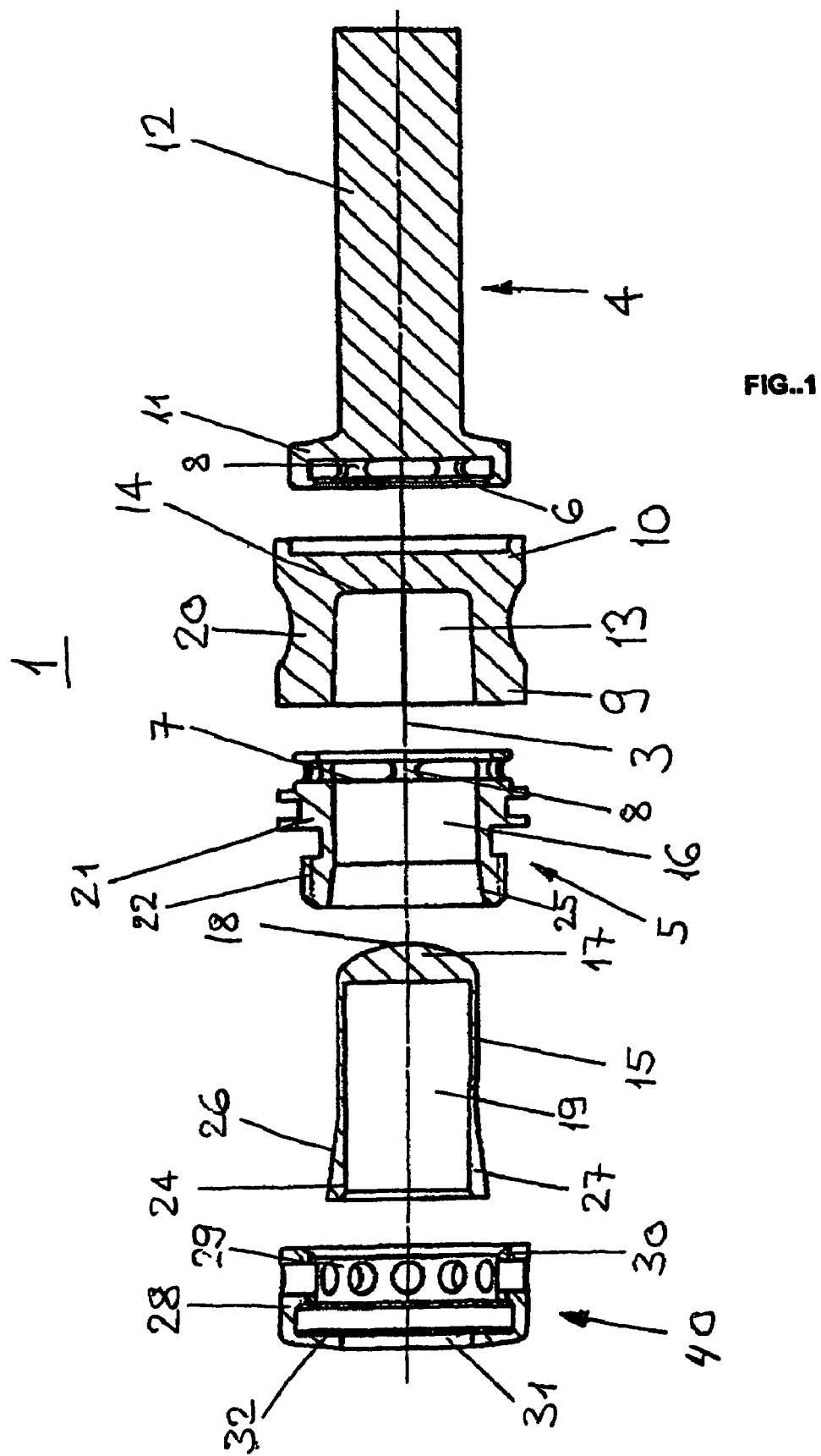
FIG..1

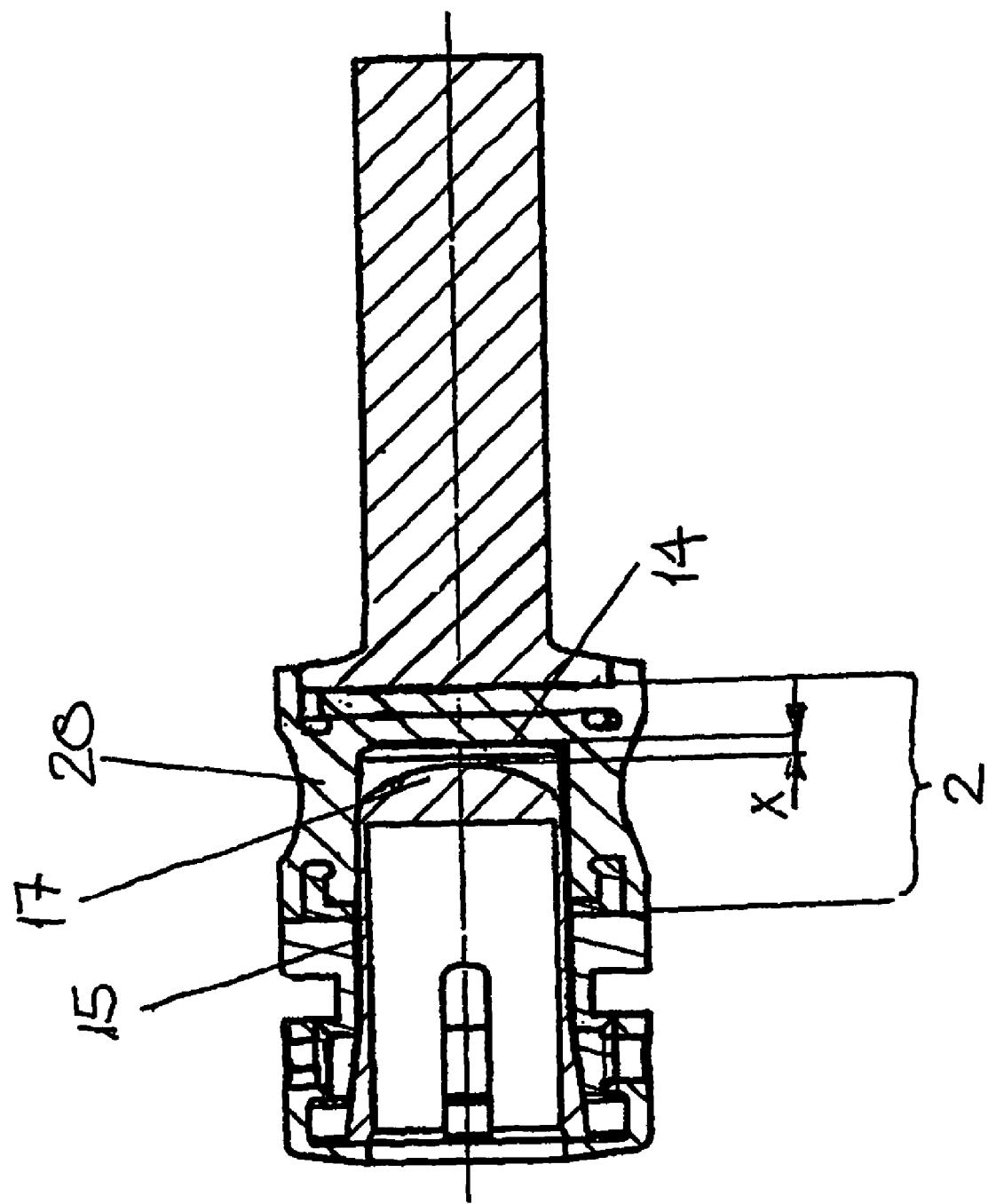
FIG..2

DYNAMIC DAMPING ELEMENT FOR TWO BONES

CROSS REFERENCE TO RELATED APPLICATION

This is a continuation of International Patent Application No. PCT/CH2003/00649, filed Sep. 29, 2003, the entire contents of which are incorporated herein by reference thereto.

TECHNICAL FIELD OF THE INVENTION

The invention is directed to a damping element having a generally cylindrical flexible element with dynamically changing damping characteristics.

BACKGROUND OF THE INVENTION

Damping elements that can be used, for example, as a connecting element between two adjacent pedicle screws within a fixing device for the spinal column are known. Such known damping elements comprise essentially two axially external longitudinal connecting elements and a part provided between them, that is made from a material having a greater elastic deformability than the external connecting elements. A disadvantage of this known damping element is that the spring characteristics of the middle, elastic part is determined by the geometry and the choice of material.

SUMMARY OF THE INVENTION

The object of the invention is to produce a damping element with progressive spring characteristics, the progression of which can be selected.

In particular:
progressive spring characteristics can be set, assuring an adequately great elastic flexibility in the case of small spring travels. Thus, adequate freedom of movement of the spinal column is possible in this region;
in the case of an adjustable spring travel, a greater resistance occurs, so that an overload of the posterior elements can be avoided; and
no overloads on the bodies of the vertebra or on the intervertebral disk, lying in the intervertebral space, will occur even in the case of impact loads.

The damping element has a flexible spring element and a clamping sleeve inserted into the spring element. The dimension X between an internal wall of the flexible element and the front end of a clamping sleeve is preferably between 0-2 mm. By virtue of this, the spring travel of the spring element can be set with the spring characteristics of $f_1$. As soon as the spring element is axially compressed by the dimension X, the front end of the clamping sleeve, introduced into the hollow space of the spring element, abuts against the face of the hollow space, so that during a further axial compression of the spring element the end wall in the hollow space of the spring element will be deformed and thus a greater spring characteristics $f_2$ will prevail.

The flexible element is made preferably from an elastomer, whereas the clamping sleeve is manufactured preferably from a metallic material, particularly from titanium.

In another embodiment, the front end of the clamping sleeve has a convex construction. Spring characteristics $f_2$ can be influenced by the shape of the convex face on the front end of the clamping sleeve, so that, for example, by virtue of a flat convex face a stronger progression of the spring characteristics $f_2$ can be achieved than would be the case with a convex face having a greater curvature.

In yet another embodiment, the connecting parts are joined with the spring element rotatably and axially form-locked. For this purpose the connecting parts preferably have tabs on their faces, directed towards the spring element, and the tabs could be cast into the ends of the spring element.

In a further embodiment, the connecting part comprises externally a rod that is coaxial with the longitudinal axis, by virtue of which the damping element can be joined, for example, with a bone anchoring element.

In yet another further embodiment, the second connecting part is constructed as a bushing with a central bore that is coaxial with the longitudinal axis, while the clamping sleeve can pass through the central bore, at least partially. The locking of a rod-shaped longitudinal support in the clamping sleeve is carried out preferably by wedging an internal taper provided in the central bore of the bushing into a complementary external taper on the clamping sleeve. For the purpose of accepting a rod-shaped longitudinal support of an osteosynthetic stabilizing device, the clamping sleeve has a coaxial blind hole open at the rear end.

In another embodiment, the radial elastic deformability of the clamping sleeve is achieved by at least one slot radially penetrating the wall of the clamping sleeve. The compression of the clamping sleeve is carried out by a thread provided on the bushing, over which a locking means, preferably constructed as a nut, can be screwed.

BRIEF DESCRIPTION OF THE DRAWINGS

The detailed description will be better understood in conjunction with the accompanying drawings, in which like reference characters represent like elements as follows:

FIG. 1 is an exploded, cross-sectional view of an embodiment of a damping element, and FIG. 2 is a cross-sectional view of the assembled damping element of FIG. 1.

DETAILED DESCRIPTION OF THE INVENTION

FIGS. 1 and 2 show an embodiment of a damping element 1 with a longitudinal axis 3, an external longitudinal connecting part 4, an axially opposed external hollow body-shaped connecting part 5 and an elastic means 2 provided coaxially between them.

The hollow body-shaped connecting part 5 is constructed as a hollow cylindrical bushing 21 and has an outside diameter corresponding to that of the elastic middle part 2. The longitudinal connecting part 4 comprises axially externally a cylindrical rod 12 and a flange 11 bordering the elastic middle part 2, the outside diameter of the flange corresponding approximately to that of the elastic middle part 2. The hollow body-shaped connecting part 5 has a first face 7 which is directed towards the elastic middle part 2 and is perpendicular to the longitudinal axis 3. Similarly to that, the flange 11 has a second face 6 which is directed towards the elastic middle part 2 and is perpendicular to the longitudinal axis 3.

The faces 6, 7 on the connecting parts 4, 5, directed towards the elastic middle part 2, are provided with tabs 8, which are arranged circumferentially on a circle concentrically with the longitudinal axis 3. The tabs 8 are cast during the manufacture of the longitudinal support 1 into the external ends 9, 10 of the elastic middle part 2, so that an axial and rotational form-locking is produced between the elastic middle part 2 and the axially external connecting parts 4, 5.

The elastic middle part 2 is in this case cylindrical and comprises a flexible spring element 20 that is coaxial with the longitudinal axis 1 with an equally coaxial hollow space 13 and a clamping sleeve 15 coaxially arranged in the hollow space 13. The hollow space 13 is axially open towards the hollow body-shaped connecting part 5 and enclosed towards the longitudinal connecting part 4 with an end wall 14 that is perpendicular to the longitudinal axis 3.

The clamping sleeve 15 can be axially introduced into the central bore 16 in the hollow body-shaped connecting part 5 as well as the hollow space 13. In the embodiment illustrated here the clamping sleeve 15 has at its front end a convex face 18 directed towards the end wall 14 of the hollow space 13, the convex face being in the non-deformed state of the elastic middle part 2 at an axial distance of X from the end wall 14 of the hollow space 13 (FIG. 2). The result of this is that under an axial load on the elastic middle part 2, this will be first deformed with the spring characteristics f, of the spring element 20. As soon as the spring element 20 is compressed axially by the dimension X, the apex of the convex face 18 at the front end 17 of the clamping sleeve 15 abuts against the end wall 14 of the hollow space 13, so that during a further axial compression of the elastic middle part 2 the end wall 14 will be deformed in the hollow space 13 of the spring element 20, and consequently a higher spring characteristics $f_2$ will prevail. This spring characteristics $f_2$ can be influenced by the shape of the convex face 18 at the front end 17 of the clamping sleeve 15, so that by virtue of a flat convex face 18 a stronger progression of the spring characteristics $f_2$ can be achieved than would be the case if the a convex face 18 would have a greater curvature. Furthermore, by virtue of the axially variable position of the clamping sleeve 15 in the hollow space 20 relative to the spring element 20, the dimension X and consequently the transition of the spring characteristics from $f_1$ of the spring element 20 to a higher spring characteristics $f_2$ of the spring element 20, abutting against the front end 17 of the clamping sleeve 18, can be adjusted.

The hollow cylindrical connecting part 5 is made in this case from two parts and comprises a bushing 21 that on its external end 23 has a thread 22. The bushing 21 has a central bore 16 that is coaxial with the longitudinal axis 3, while the central bore 16 expands into an internal taper 25 towards the external end 23 of the bushing 21. The diameter of the central bore 16 is so dimensioned, that the clamping sleeve 15 can be introduced into the central bore 16. On its rear end 24 the clamping sleeve 15 has an external taper 26, that can be wedged into the internal taper 25 in the central bore 16 of the bushing 21. The clamping sleeve 15 has a coaxial blind hole 19 that is open at the rear end 24, into which a rod-shaped longitudinal support (not illustrated) can be introduced from the rear end 24. Furthermore, the rear end 24 of the clamping sleeve 15 has at least one slot 27 that radially penetrates the wall of the inner spring element 15, so that when the external taper 26 is pressed into the internal taper 25 the rear end 24 of the clamping sleeve 15 is radially compressed and a rod-shaped longitudinal support, introduced into the blind hole 19, can be secured. The axial displacement of the clamping sleeve 15 relative to the spring element 20 is carried out by locking or fastening means 40, which is constructed in this case as a nut 28 that can be screwed onto the bushing 21 via the thread 22. The nut 28 has a coaxial bore 29 with an inside thread 30 and an axially external constriction 31. When the nut 28 is screwed on the external end 23 of the bushing 21 via the thread 22, the rear end 24 of the clamping sleeve 15 will abut against the shoulder 32 formed by the constriction 31, so that during further tightening of the nut 28 the clamping sleeve 15 is radially compressed.

The invention claimed is:

1. A dynamic damping element for interconnecting at least two bone anchors, the damping element including a longitudinal axis and a progressive spring characteristic, the damping element comprising:

a cylindrical rod having a flange formed on an end thereof, the flange including a plurality of first tabs;

a hollow cylindrical bushing including a central bore, an external thread and a plurality of second tabs disposed circumferential on an outer surface of the bushing;

a spring element coaxially aligned with the longitudinal axis of the damping element and located in-between the flange and the bushing, the spring element including a hollow space extending from a first opened end, the hollow space forming an end face, the first and second tabs engaging the ends of the spring element respectively, the spring element having an initial spring characteristic;

a clamping sleeve received within the central bore of the bushing and the hollow space of the spring element, the clamping sleeve including a convex face directed towards the end face of the hollow space, the convex face being spaced at an axial distance from the end face of the hollow space when the clamping sleeve is inserted into the hollow space of the spring element; and a nut including an internal threading to threadably engage the external thread of the bushing so that rotation of the nut causes the convex face of the clamping sleeve to contact the end face of the hollow space, which in turn causes additional axial compression of the spring element resulting in a second spring characteristic, the second spring characteristic being higher than the initial spring characteristic, wherein the central bore of the bushing includes an internal taper and the clamping sleeve includes a corresponding external taper and at least one slot, rotation of the nut farther causing the external taper of the clamping sleeve to be pressed against the internal taper formed in the central bore of the bushing so that the clamping sleeve is radially compressed.

2. The damping element of claim 1 wherein the axial distance is between 0 mm and 2 mm.

3. The damping element of claim 1 wherein the spring element is constructed of an elastomer.

4. The damping element of claim 1 wherein the clamping sleeve is constructed of a metallic material.

5. The damping element of claim 1 wherein the first and second tabs are cast.

6. The damping element of claim 1 wherein the clamping sleeve includes a blind hole open at a rear end and sized to accept a rod-shaped part.

7. The damping element of claim 1 wherein the at least one slot radially penetrates a wall of the clamping sleeve.

* * * * *